United States Patent [19]

Shochat

[11] Patent Number: 4,792,521
[45] Date of Patent: Dec. 20, 1988

[54] NON-ENZYMATIC IMMUNOHISTOCHEMICAL STAINING SYSTEM AND REAGENTS

[75] Inventor: Dan Shochat, Maplewood, N.J.

[73] Assignee: Immunomedics, Inc., Newark, N.J.

[21] Appl. No.: 766,106

[22] Filed: Aug. 15, 1985

[51] Int. Cl.$^4$ .............................................. G01N 33/53
[52] U.S. Cl. ................................................ 435/7; 435/5;
435/810; 424/3; 424/5; 424/7.1; 436/501;
436/512; 436/519
[58] Field of Search .............. 424/3, 5, 7.1; 436/501,
436/536, 539, 512, 519, 532, 904; 544/347;
435/5, 7, 26, 810, 25

[56] References Cited

U.S. PATENT DOCUMENTS

| | | | |
|---|---|---|---|
| 4,160,645 | 7/1979 | Ullman | 436/517 |
| 4,556,634 | 12/1985 | Misaki et al. | 435/25 |
| 4,598,042 | 7/1986 | Self | 436/518 |
| 4,654,300 | 3/1987 | Zuk et al. | 436/533 |

FOREIGN PATENT DOCUMENTS

| | | | |
|---|---|---|---|
| 0059677 | 5/1978 | Japan | 544/347 |
| 2083488 | 3/1982 | United Kingdom | 544/347 |

OTHER PUBLICATIONS

Weiss, L., Histology Cell and Tissue Biology, (fifth edition), Elsevier Science Publishing Co., New York, pp. 98–108, (1983).

Primary Examiner—Robert J. Warden
Assistant Examiner—Stephen C. Wieder
Attorney, Agent, or Firm—Bernhard D. Saxe

[57] ABSTRACT

A non-enzymatic method of immunohistochemical staining uses a bound electron transfer agent to achieve amplification of antibody binding to specific antigens of interest in a histology or cytology specimen. A preferred embodiment uses a bound phenazine, which is reduced with a soluble reducing agent, and which in turn reduces a tetrazolium salt, to precipitate a formazan dye at the site of primary antibody binding to the antigen of interest. Reagents and kits for use in the method are also provided.

25 Claims, No Drawings

NON-ENZYMATIC IMMUNOHISTOCHEMICAL STAINING SYSTEM AND REAGENTS

BACKGROUND OF THE INVENTION

This invention relates to an immunohistochemical method for staining histology or cytology specimens using non-enzymatic reagents which, nevertheless, provide a means for amplifying the detection of bound antibody to a cellular component by converting a plurality of molecules of a soluble chromogen to an insoluble chromophore, which deposits at the site of the component.

Histochemical techniques were developed to permit selective staining of particular cellular components, e.g., molecular species, in tissue or other histological specimens by virtue of unique physicochemical properties thereof. Immunohistochemical methods take advantage of the ability of specific antibodies to bind to cellular components and to other antigens, e.g., viral, bacterial, fungal or parasitic antigens and/or products of cells or microorganisms. The antibodies are tagged with labels to render them detectable, e.g., radioisotopes, fluorescent compounds, chromophores, enzymes and the like. The use of enzymes has the further advantage that it serves to amplify the detection reaction by catalyzing the conversion of many substrate molecules to produce molecules which, in turn, serve to promote the conversion of many molecules of a soluble chromogen to insoluble chromophores which then precipitate at the site of binding of the specific antibody.

Further modifications of this technique have used enzymes conjugated to second antibodies, which bind to the primary antibodies that recognize the cellular components. Other modifications have been primary antibodies conjugated to biotin or avidin, with enzymes conjugated to the other member of this pair. Such enzyme-linked staining techniques and reagents are reviewed in Primus et al., "Functional Histopathology of Cancer: A Review of Immunoenzyme Histochemistry", In *Methods of Cancer Research*, 20, 139–182 (Academic Press, New York, N.Y., 1982), and are familiar to the skilled artisan in this field.

The most commonly used enzymes in this technique have been peroxidases, glucose oxidase and phosphatases. Peroxidases typically operate by using hydrogen peroxide to oxidize a iron porphyrin bound to the enzyme. The oxidized cofactor in turn oxidizes a soluble chromogen, typically diaminobenzidine (DAB), aminoethylcarbazole, 4-chloro-1-naphthol, tetramethyl-benzidine or phenylenediamine/pyrocatechol, to form an insoluble dye, which deposits at the site of bound antibody to which the enzyme is directly or indirectly bound or linked through one or more bridging antibodies or other specific binding couples, e.g., an avidin-biotin couple.

Glucose oxidase typically operates by using a substrate, normally glucose, to reduce a bound cofactor, e.g., NAD+, which in turn reduces an electron transfer agent, e.g., phenazine methosulfate (PMS), and is itself reoxidized. The reduced electron transfer agent then reduces a soluble chromogen, e.g., a tetrazolium salt, to an insoluble dye, e.g., a formazan, which deposits at the site of bound antibody. In this variant, the electron transfer agent is added in soluble form and mediates electron transfer from the redox cofactor of the enzyme to the soluble chromogen.

Phosphatases typically operate by hydrolyzing a substrate which is a phophate ester of a substituted naphthol, e.g., naphthol AS phosphate (3-hydroxy-2-naphthoic acid anilide phosphate). The free napthol then reacts with a stable solubel diazotate in the developing solution, e.g, Fast Blue or Fast Red, forming an insoluble dye.

Another powerful advance involves the use of soluble immune complexes of the enzyme, e.g., a peroxidase/anti-peroxidase (PAP) complex, by which the enzyme is bound to the site of bound specific antibody through the intermediacy of a bridging antibody. Typically, the PAP complex uses antibodies of the same species as the primary antibody, and the bridging antibody is an anti-species antibody from another animal. For example, if the primary antibody and the anti-peroxidase are both murine antibodies, the bridging antibody could be goat anti-mouse IgG. This techniques has the advantage that it does not require covalent binding of the enzyme to an antibody or to another carrier or hapten.

However, enzymes have relatively limited stabilities, and they are stable over a relatively narrow range of conditions. In contrast, immunoglobulins are far more stable. Thus, an immunohistochemical reagent that contains an enzyme component has a limited shelf life primarily because of the presence of the enzyme. Furthermore, the fragility of the enzyme could limit the conditions under which it can be coupled to antibody or other linker.

A need therefore continues to exist for immunohistochemical reagent systems which embody the amplification which enzymes can impart, but which are enzyme-free and have longer shelf life and greater stability.

OBJECTS OF THE INVENTION

One object of the present invention is to provide an improved immunohistochemical method using enzyme-free reagents for staining tissue specimens.

Another object of the invention is to provide a visual immunohistochemical method wherein background staining is significantly reduced.

A further object of the invention is to provide an immunohistochemical method having significantly increased specificity, sensitivity and simplicity.

Yet another object of the invention is to provide improved, enzyme-free immunohistochemical reagents and kits having longer shelf life and greater stability than enzyme-containing reagents.

Upon further study of the specification and appended claims, further objects and advantages of this invention will become apparent to those skilled in the art.

SUMMARY OF THE INVENTION

The foregoing objects can be achieved by providing, in an immunohistochemical method for staining a histology or cytology specimen to reveal the presence therein of at least one immunologically detectable antigen, wherein (1) the sample is contacted with a solution of a primary antibody or antibody fragment which specifically binds to the antigen, (2) unbound primary antibody/ fragment is removed, and (3) the presence of bound primary antibody/fragment is revealed as a stain by reaction with a staining reagent system capable of transforming a chromogen to a colored dye which precipitates at the site of the bound primary antibody/fragment, the improvement wherein the primary antibody/-fragment is directly or indirectly conjugated, or linked through one or more bridging antibodies or other specific binding couples, to an electron transfer agent capable of transforming the chromogen to a dye in the presence of a soluble oxidizing or reducing agent; and wherein the staining reaction effected by the staining reagent system is effected without the use of an enzyme.

The invention also provides reagents and kits for use in practicing the foregoing method.

DETAILED DISCUSSION

The general method of the invention can be embodied in a number of alternative combinations, each of which represents a different balance between ease of preparation of reagents, total staining time, convenience in handling the system, and the possibility or impossibility of using a universal developing system.

Unless otherwise noted, use of the term "antibody" herein will be understood to include antibody fragments and thus to be equivalent to the term "antibody/fragment" which is used interchangeably therefor in this discussion. Antibodies can be whole immunoglobulin of any class, e.g., IgG, IgM, IgA, IgD, IgE, or hybrid antibodies with dual or multiple antigen or epitope specificities, or fragments, e.g., F(ab')$_2$, F(ab)$_2$, Fab', Fab and the like, including hybrid fragments.

Antibodies include antiserum preparations, preferably affinity-purified, having a high immunoreactivity, e.g., a binding constant of at least about $10^7$ l/mole, preferably at least about $10^9$ l/mole, a high immunospecificity, e.g., at least about 40%, preferably at least about 60%, more preferably about 70–95%, and a low cross-reactivity with other tissue antigens, e.g., not more than about 30%, preferably not more than about 15% and more preferably not more than about 5%. The antiserum can be affinity purified by conventional procedures, e.g., by binding antigen to a chromatographic column packing, e.g., sephadex, passing the antiserum through the column, thereby retaining specific antibodies and separating out other immunoglobulins and contaminants, and then recovering purified antibodies by elution with a chaotropic agent, optionally followed by further purification.

Monoclonal antibodies are also suitable for use in the present method, and are preferred because of their high specificities. They are readily prepared by what are now conventional procedures of immunization of mammals with an immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the tissue specificity of the antibodies that affects their utility in the present method.

Antibody fragments can be made by pepsin or papain digestion of whole immunoglobulins by conventional methods such as those disclosed, inter alia, in U.S. Pat. No. 4,331,647.

One important application of the present method is immunohistochemical examination of the biopsy samples using antibodies to tumor-associated antigens. Many antibodies and antibody fragments which specifically bind markers produced by or associated with tumors or infectious lesions, including viral, bacterial, fungal and parasitic antigens and products associated with such microorganisms have been disclosed, inter alia, in Hansen et al., U.S. Pat. No. 3,927,193 and Goldenberg, U.S. Pats. Nos. 4,331,647, 4,348,376, 4,361,544, 4,468,457, 4,444,744, 4,460,459 and 4,460,561, and in related pending applications U.S. Ser. Nos. 609,607, abandoned and 633,999, U.S. Pat. No. 4,624,846 the disclosures of all of which are incorporated herein in their entireties by reference. It will be appreciated that the present method is also applicable to revelation of normal histological structures using antibodies thereto, such antibodies being available or readily made by conventional immunological techniques.

Antibodies which specifically bind the electron transfer agent and/or conjugates thereof can be readily obtained by conventional techniques. Polyclonal antibodies can be made by immunizing an animal, e.g., a mouse, rabbit, goat, donkey and the like, with the electron transfer agent itself or an immunogenic conjugate thereof, e.g., a conjugate with bovine serum albumin (BSA), or a conjugate with an oligomer such as one of those disclosed below. The hyperimmune serum is collected and conventionally processed to recover specific antiserum. Monoclonal anti-electron transfer agent antibodies can be prepared conventionally by analogy to the methods described hereinabove for preparing other monoclonal antibodies.

In a first embodiment of the present method, an electron transfer agent is directly bound to the primary antibody or antibody fragment which specifically binds to the tissue component of interest for staining. This has the distinct advantage of requiring only a single antibody incubation step for developing the stain and therefore staining can be effected in the shortest time.

The electron transfer agent can be indirectly bound to the primary antibody. By "indirectly bound" is meant herein covalently linked through a short or long linker moiety which is joined to one molecule or a plurality of molecules of the electron transfer agent through one or more functional groups and which is conjugated to the antibody through functional group linkages to, e.g., antibody amine, carboxyl, phenyl, thiol or hydroxyl groups. One embodiment of this approach is to covalently bind a plurality of electron transfer agent molecules to an oligomer, e.g., a polyamide, a polyester, a polyacrylate, a polyvinyl alcohol, a polyvinylamine, a poly(aminodextran) or the like. Any oligomer having a plurality of functional groups capable of forming a covalent bond with a molecule of the electron transfer agent can be used, although some are more advantageous than others.

Suitable oligomers advantageously have a molecular weight from about 5,000 to about 1,000,000 daltons, preferably about 25,000–300,000 daltons. A lower molecular weight oligomer would not have enough functional groups for attachment of electron transfer agents, although it is not excluded per se. Similarly, an oligomer or polymer with a molecular weight much higher than 1,000,000 daltons, while not excluded per se, may compromise the immunoreactivity and the solubiltiy of the antibody to which it is conjugated.

The oligomers will advantageously contain an average of about 2–500 points for attachment of electron transfer agent molecules and/or linker groups, preferably about 50–200 points. There can be more points for attachment of electron transfer agents, and/or for biotin or other components of specific binding couples, or for attachment of linkers for antibody conjugation. However, it is unlikely that attachment of more than about 500 electron transfer molecules will significantly enhance staining efficiency.

The oligomers can be homopolymers or copolymers and can contain one or several kinds of groups for attachment of electron transfer agents and/or linkers. Comonomers which improve their solubility and/or stability or confer other desirable properties upon the oligomers can also be incorporated.

Suitable polyamides include oligomers comprising amino acids having pendant functional groups, such as polylysine, polyglutamate or a polypeptide comprising lysine and/or glutamate residues. A number of such polyamide oligomers are commercially available, e.g., polylysine having an average molecular weight in the ranges of 30,000–70,000 daltons or 150,000–300,000 daltons, poly(lysine, alanine) having an average molecular weight of 20,000–50,000 daltons and an average lysine content of 50–70% by weight, poly(glutamate, alanine) having an average moleclar weight of 20,000–50,000 daltons and an average glutamate content of about 70%.

Electron transfer agent molecules can be linked through amide bonds using an amine substitutent on the agent, which is coupled to a carboxyl group on the oligomer, e.g., using a carbodiimide coupling agent such as dicyclohexylcarbodiimide (DCC). Similarly, a carboxyl on the electron transfer agent can be bound to a polysine using DCC as the coupling agent. The charged oligomer can then be bound to the antibody by coupling unreacted lysyl amines to antibody carboxyl groups with DCC, although this approach to antibody conujugation often leads to significant cross-linking of antibody and aggregation.

Alternatively, the terminal amine can be protected, e.g., as the t-butyloxycarbonyl (Boc) derivative, uncharged lysyl amines can be capped with, e.g., acetic anhydride, and the terminal amine can then be deprotected and converted to e.g., an isothiocyanate by reaction with, e.g., p-isothio-cyanatobenzoyl chloride or the corresponding anhydide. The foregoing procedure has the further advantages that subsequent linkage with antibody occur at only one point on the charged oligomer, and by a method which minimizes cross-linking and aggregation of the antibody.

Another attractive method of conjugation which avoids cross-linking and aggregation is treatment of the antibody with an activated maleimide to convert pendant amines to maleimides, treatment of an oligomer containing electron transfer agent molecules, or the electron transfer agent itself, with a reagent which links sulfhydryl groups to the oligomer or agent, and reaction of the maleimidoantibody with the thiolated oligomer or agent to form sulfide-bridged conjugates.

As noted earlier, binding the electron transfer agent to the primary antibody has the disadvantage that a universal developing system is precluded. One alternative embodiment which avoids this problem, at the expense of additional incubation steps and attendant longer staining times, uses primary antibody conjugated to biotin or avidin. The electron transfer agent is then conjugated to the other component of the biotin/avidin couple. Another alternative is to biotinylate both the primary antibody and the electron transfer agent and include an intermediate incubation of the bound primary antibody with avidin. This alternative includes the possibility of conjugating a plurality of electron transfer agent molecules to an oligomer, which is then conjugated to one or a plurality of biotin molecules, and reacting the resultant conjugate with avidin-conjugated primary antibody or with biotinylated primary antibody after the latter has bound to tissue and has been incubated with avidin.

The foregoing embodiments all require that the primary antibody be conjugated to some other function. This can be avoided in embodiments using secondary antibodies which specifically bind the species of antibody used for the primary antibody. For example, if the primary antibody is a mouse IgG, the secondary antibody can be a goat anti-mouse IgG, a rabbit anti-mouse IgG and the like. Many of these anti-species immunoglobulins are available commercially. Furthermore, their use permits the design of other types of universal developing systems.

One approach is to bind the electron transfer agent directly or indirectly to the secondary antibody, again including the use of a charged oligomer conjugate. This has the advantage of using only two antibody binding incubations. An attractive variant of this approach is to use a F(ab')$_2$ fragment of the secondary antibody, and conjugate it to a polylysine charged with a plurality of molecules of the electron transfer agent and capped with an isothiocyanate linker. The resultant conjugate would function as a universal developing agent component which would significantly amplify the antigen-antibody binding reaction on the tissue sample while, at the same time, having a comparable molecular weight to whole IgG.

Another alternative embodiment is to use a biotinylated secondary antibody, of which many are available commercially, in conjunction with an avidin-conjugated electron transfer agent or with avidin and a biotin-conjugated electron transfer agent, including an oligomer charged with a plurality of molecules of electron transfer agent and capped with one or a plurality of biotin molecules.

All of the foregoing share the requirement that the electron transfer agent be conjugated to some component of an immune pair or an analogous specific binding couple. An alternative embodiment which avoids even this requirement uses an oligomer or other suitable carrier, charged with a plurality of molecules of the electron transfer agent, but supplied to the staining system as a soluble immune complex with anti-(electron transfer agent conjugate) antibodies, similar to the PAP or glucose oxidase/anti-glucose oxidase (GAG) complexes known in the prior art. This will be denoted hereinafter as a "MAM" complex, for mediator/anti-mediator complex, the mediator being the electron transfer agent.

Antibodies which specifically bind the electron transfer agent can be produced by using the charged oligomer conjugate thereof as an antigen and challenging the species of animal used to make primary antibody, after which antiserum is recovered containing anti-mediator antibodies. The antiserum is used to produce MAM immune complex by minor modification of the conventional procedures for producing PAP and GAG immune complexes. See, e.g., Sternberger, "Immunochemistry", pp 123–171 (Prentice-Hall, Englewood Cliffs, N.J., 1974); Clark et al., *J. Histochem. Cytochem.*, 30, 27 (1982). Briefly, the equivalence point of an antiserum containing antibodies which specifically bind the electron transfer agent and/or its conjugate ("antigen" for this limited discussion) is determined by precipitation with the conjugate or antigen. The antiserum is then incubated with a slight excess of antigen, the immune precipitate is isolated, resuspended in a significant excesss of antigen, solubilized at low pH and purified.

It will be appreciated that the foregoing embodiments represent only illustrative possibilities and by no means exhaust the manifold permutations available for practicing the method of the invention. Other alternatives, including multiple bridging antibodies and use of a variety of other carriers and linkers for the electron transfer agent, can be envisioned by the skilled artisan and are substantially equivalent to the embodiments described hereinabove.

Many types of electron transfer agents can be used in the present method. Their essential function is to mediate oxidation of oxidizable chromogens or reduction of reduceable chromogens to form insoluble dye molecules at the site of binding of the primary antibody, corresponding to the location of the specific tissue component to which it binds. This is effected by supplying the system with a soluble component which forms a redox couple with the electron transfer agent, and also supplying a soluble chromogen which in turn forms a redox couple with the product of the first redox reaction and is converted to an insoluble dye. It is necessary that the soluble redox component not react directly with the soluble chromogen at any appreciable rate, otherwise dye will form at other than the site of bound mediator.

Earlier staining systems using soluble electron transfer agents as mediators for the transfer of electrons between an enzyme substrate and a chromogen suffered from the problem that, after the electron transfer between enzyme and mediator, the mediator could diffuse away from the enzyme before effecting an electron transfer between itself and and the chromogen. Thus, for example, Clark et al., J. Histochem. Cytochem., 30, 27–34(1982), reported that use of more than an optimum concentration of phenazine methosulfate (PMS), or too early addition of PMS to the glucose substrate and p-nitro blue tetrazolium used to develop a glucose oxidase slide, caused the deposit of a blue-flecked film on the sections in addition to the deposited formazan dye at the specifically stained sites.

Use of a bound mediator in the present method prevents adventitious migration of reduced or oxidized mediator from the site of bound antibody prior to transfer of electrons between the mediator and the chromogen. This makes the present method less sensitive to reagent concentrations and other procedural variables. Moreover, use of an oligomer charged with a plurality of electron transfer agent molecules, but bound to the site of specific antibody binding, improves the staining definition by avoiding diffusion of the mediator and ensuring deposition of dye at the precise location of the tissue whose detection is desired. It also provides additional amplification of the development reaction. Even use of avidin together with biotin-conjugated electron transfer agent provides some amplification, because of the tetravalency of avidin, without losing definition in the stained areas.

Among the reducing systems which can be envisioned, an attractive combination includes a bound phanazine as mediator, a soluble reducing agent for the phenazine, and a soluble chromogen which is reduced by reduced phenazine. For example, a phenazine can be used having the formula;

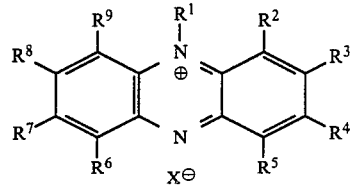

wherein $R^1$ is alkyl, cycloalkyl, aralkyl or L; X is one equivalent of a counteranion; $R^2$–$R^9$ are each independently H, alkyl, cycloalkyl, aryl, aralkyl, alkaryl, OH, $OR^1$, SH, CN, $NH_2$, $NHR^1$, $NR^1_2$, $NO_2$, F, Cl, Br, I, $SO_3$, $COOR^1$, or $R^2$ and $R^3$, $R^3$ and $R^4$, $R^4$ and $R^5$, $R^6$ and $R^7$, $R^7$ and $R^8$, or $R^8$ and $R^9$, taken together with the carbon atoms to which they are joined form a benzene ring, or one of $R^2$–$R^9$ is L; and L is a divalent linking function joining the phenazine ring system to said primary antibody or to said bridging antibody or specific binding couple component, or to an oligomeric carrier which is a component of an immune complex.

In the foregoing formula, suitable alkyl groups include any linear or branched alkyl group of 1–30 carbon atoms, preferably 1–18 carbon atoms, and more preferably lower alkyl, especially methyl and ethyl. Suitable cycloalkyl groups include monocyclic or polyclic carbocyclic ring systems having 3–30 carbon atoms, preferably 3–18 carbon atoms, more preferably cyclopentyl, cyclohexyl and cyclopropyl, and optionally linked to the phenazine nucleus, i.e., to a ring nitrogen or to a heteroatom of a ring substituent, by a linear or branched alkylene moiety of 1–10 carbon atoms. Suitable aralkyl groups include a linear or branched alkylene moiety of 1–10 carbon atoms bound at one terminus to the phenazine nucleus, i.e., to a ring nitrogen or to a heteroatom of a ring substituent, and at the other terminus to a monocyclic or polycyclic carbocyclic aromatic ring or to an inert heteroaromatic ring, i.e., one which does not interfere with the redox reactions mediated by the phenazine. Preferred such aralkyl groups include benzyl and phenethyl. The foregoing substituents may be further substituted with other groups which do not interfere with the redox reactions, e.g., halogens, nitro, cyano, alkoxy and the like.

Suitable substituents for $R^2$–$R^9$ can include, in addition to H, any of the foregoing alkyl, cycloalkyl and aralkyl groups, as well as aryl and alkaryl groups, and any other noninterfering substituents, e.g., halogen, $NO_2$, CN, OH, $OR^1$, $NH_2$, $NHR^1$, $NR^1_2$, COOH, $COOR^1$, $CONH_2$, $SO_3H$ and the like, optionally joined to the ring through a linear or branched alkylene moiety of 1–10 carbon atoms. Suitable aryl groups include any monocyclic or polycyclic carbocyclic aromatic rings, and heteroaromatic rings containing non-interfering groups, preferably having 1–30 carbon atoms, more preferably 1–12 carbon atoms, especially phenyl. Suitable alkaryl groups include any of the foregoing aryl groups substituted by lower alkyl or the like.

Suitable counteranions include common conjugate anions of mineral acids or other strong acids, e.g., chloride, nitrate, sulfate, perchlorate, methane-sulfonate, toluenesulfonate and the like, conjugate anions of weak acids, e.g., benzoate, acetate, citrate and the like, anions of long chain fatty acids, e.g., palmitate, oleate and the like, anions of alkylsulfonic acids, e.g., dodecylsulfonate and the like, or any other counteranion that does not interfere with the redox function of the phenazine.

The phenazine is linked to antibody or other component of a specific binding couple, such as biotin or avidin, or to oligomer through a linking function, denoted by L. This can be simple amine, carboxyl, hydroxyl, thiol or sulfonic acid substituent on the ring or joined to the ring system by a bridging group, e.g., a linear or branched alkylene group having 1–30 carbon atoms, and optionally substituted with non-interfering substituents.

Simple ring substituents can be transformed into more reactive substituents or ones which react under milder conditions or more selectively. For example, an amine can be reacted with thiophosgene to convert it into an isothiocyanate. An amide can be subjected to a Curtius rearrangement and converted to an isocyanate. Many other such functional group transformations are familiar to the ordinary skilled artisan and can be used to vary the linking functions.

It is also possible to effect functional group conversions by means of intermediate linking moieties. For example, an amine can be reacted with 2-iminothiolane, and the resultant thiolated moiety can be reacted with an antibody or an oligomer bearing maleimide groups.

Another useful linking moiety is p-bromomethylbenzoic acid, useful for reaction with phenazine to form a carboxyl-substituted N-benzylphenazonium salt. An amine can be reacted with succinic anhydride to interpose a monosuccinamide and present a carboxyl group for reaction with e.g., the amine of a lysyl residue.

An amine substituent on the phenazine can also be reacted with the carboxyl or biotin in the presence of DCC. Biotin N-hydroxysuccinimide ester is available commercially and is a convenient alternative to the DCC-activated form. Or biotin/DCC ca be added to a polylysine before, after or together with a carboxyl-substituted DCC-activated phenazine. The latter approach is attractive in the embodiment wherein biotinylated second antibody is used as a component of a universal developing system, followed by avidin incubation, and then incubation with a biotinylated oligomer, especially a polylysine or a polypeptide comprising lysine residues, and charged with phenazines.

Phenazines can be synthesized by several general methods, among which are reaction of a nitrobenzene with an aniline, in the presence of hydroxide ion (Equation 1), and reaction of an o-quinone (or a pyrocatechol in air) with an o-phenylenediamine (Equation 2).

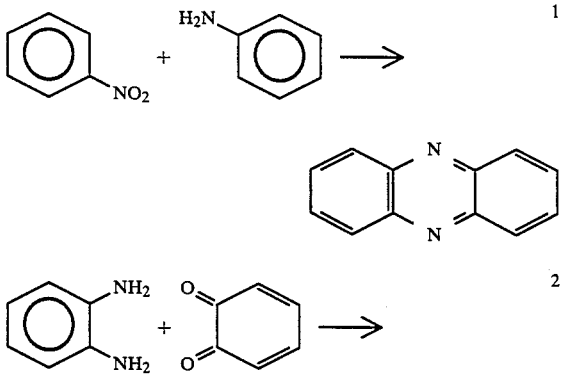

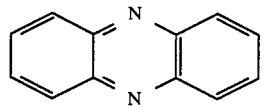

Either or both of these methods can be used to synthesize a variety of substituted phenazines which can serve as intermediates for production of phenazonium chromogens for eventual conjugation to antibodies and/or polymer carriers.

For example, phenazine-1-carboxylic acid is produced by fusion of nitrobenzene, anthranilic acid and potassium hydroxide, as disclosed by Birkofer, *Chem. Ber.*, 80, 212 (1947). Phenazine 1,5- dicarboxylic acid is prepared by analogous fusion of o-nitrobenzoic acid, anthranilic acid and potassium hydroxide, as disclosed by Birkofer et al., *Chem. Ber.*, 86, 1295 (1953)[*Chem. Abstr.*, 49, 1734]. These authors also describe the synthesis of benzo[a]phenazine-11-carboxylic acid by fusion of beta-naphthylamine with o-nitrobenzoic acid, the synthesis of a mixture of ethyl benzo[a]phenazine-(9 and 10)-carboxylates by condensation of 1,2-naphthoquinone with ethyl 3,4-diaminobenzoate, and synthesis of benzo[a]phenazine-(9 or 10)-propionic acid by condensation of 1,2-naphthoquinone and 3,4-diaminohydrocinnamic acid. In addition, these authors describe the conversion of phenazinecarboxylic acids to the corresponding aminophenazines by first converting the carboxyl group to a carboxamide, and then reacting the amide with bromine and base to effect a Hofmann degradation to the amine.

1-Methylphenazine can be synthesized by heating o-toluidine, nitrobenzene and KOH in hot toluene, with slow removal of water. 2-Methylphenazine can be synthesized by heating pyrocatechol and 3,4-diaminotoluene in a sealed tube and air-drying the resultant 2-methyldihydrophenazine. Each can be oxidized to the respective aldehyde with selenium dioxide, as disclosed by Rozum, *Chem. Abstr.*, 50, 3462.

2-Phenazinesulfonic acid can be synthesized by sulfonation of phenazine with oleum containing 50% $SO_3$, as disclosed by Maffei, *Chem. Abstr.*, 45, 9064. This author also discloses the synthesis of 2-cyanophenazine by heating Na 2-phenazinesulfonate with KCN. The nitrile can be hydrolyzed to the corresponding phenazine-2-carboxylate with base. Conversion of the carboxylic acid to the corresponding urea, followed by heating, produces 2-aminophenazine.

Methosulfates of a number of substituted phenazines are readily available, as shown by the disclosures of Vivian, *J. Org. Chem.*, 21, 822 and 824 (1956), and references cited therein. Representative of these are 2-chlorophenazine methosulfate and 2-chloro-8-methoxyphenazine methosulfate.

Interestingly, a number of phenazines are produced by microorganisms, and some have antibiotic properties. Representative of these are aeruginosin A (N-methyl 7-aminophenazine-1-carboxylate betaine), iodinin (phenazine-1,6-diol-5,10-dioxide), tubermycin B (phenazine-1-carboxylic acid) and pyocyanin (phenazine-1-oxide methosulfate). Several others have been identified.

Holliman and his group have synthesized a number of aminophenazines, as disclosed in *Tetrahedron*, 18, 1095 (1962); Id., 19, 1841 and 1903 (1963), and references cited therein.

General reviews of phenazine chemistry are found in Weissberger, Ed., "The Chemistry of Heterocyclic Compounds", Vol 11 (Interscience, New York, 1958); and Rodd, Ed., "Chemistry of Carbon Compounds", Vol IVC, pp 1535–1553 (Elsevier, Amsterdam, 1960).

Phenazines can be converted to their N-alkyl or N-aralkyl phenazonium (phenazinium) salts by reaction with dialkyl sulfates, alkyl or aralkyl sulfonates and the like alkylating agents.

A number of phenazines are available commercially and can be used or readily modified for linkage to antibody, biotin, avidin or oligomeric carrier or linker. Suitable such available phenazines include e.g., Safranine, Neutral Red, Rosinduline 2G, Rosinduline B, Azocarmine B, Azocarmine G, Neutral Violet and the like, in addition to phenazine and phenazine methosulfate.

Modification of the phenazine ring system can be effected by conventional aromatic substitution reactions. Alternatively, conventional aromatic substitution can be effected on the benzenoid precursors in the general synthetic methods mentioned hereinabove, prior to condensation to form the phenazine ring system.

Preferred phenazines are those wherein $R_1$ is methyl, ethyl or benzyl; one of $R^2$–$R^9$ or a substituent on the benzyl is an amine, a carboxyl, or an isothiocyanate, more preferably one that is separated from the ring system by an alkyl chain of one or more carbon atoms so as to avoid affecting the redox potential of the aromatic ring system, and the remaining R's are H; and $X^-$ is one equivalent of sulfate, chloride, methanesulfonate or toluene-sulfonate.

Soluble organic reducing agents for phenazines include dihydropyridines, e.g., reduced nicotinamide adenine dinucleotide (NADH), reduced nicotinamide adenine dinucleotide phosphate (NADPH) and the like. Inorganic reducing agents include dithionate and the like.

The type of soluble reducing agent which can be used will depend to some extent on the type of substitutents on the phenazine, since they may affect the redox potential and/or the rate of reduction. Bulky substituents may hinder approach of the reducing agent to the phenazine and interfere with reduction.

Tetrazolium salts are preferred chromogens for phenazine-mediated color development. They are not reduced at an appreciable rate by dihydropyridines such as NADH, but reduce rapidly with reduced phenazines. Tetrazolium salts such as p-nitro blue tetrazolium (NBT) are reduced from a yellow water-soluble salt to a deep blue-purple insoluble formazan dye, which precipitates at the site of bound phenazine, in the presence of reducing agent.

Amplification results from reduction of several tetrazolium salts by the same phenazine. Further amplification, or intensification of the stain, results from binding a plurality of electron transfer agent molecules to the site of antibody binding, either through a charged oligomer or through biotinylation of the electron transfer agent and a secondary or primary antibody, with avidin treatment prior to contact with the electron transfer agent moiety.

Conventional staining protocols are used for the method of the invention. See, e.g., Primus et al., "Methods in Cancer Research", Vol. 20, pp 139–182 (Academic Press, New York, N.Y., 1982). Generally, staining can be effected by a direct or indirect method, i.e., a method wherein the electron transfer agent is bound to the primary antibody or a method wherein the electron transfer agent is bound to the site to which the specific antibody is bound by means of one or more intermediate antibodies or other specific binding couples.

A tissue section, advantageously about 5 u in thickness, is prepared by, e.g., paraffin treating a formalin-fixed or ethanol-fixed specimen, or freezing a fresh, ethanol-fixed specimen. The section is first incubated for about 12–40 min, preferably about 20–30 min, at about 37° C., with a solution of about 10 ug/ml of specific antibody. Concentrations of specific antibody of from about 0.1 ug/ml to about 100 ug/mg can be used, preferably about 5–15 ug/ml. The sections are then rinsed, e.g., with phosphate-buffered saline (PBS), pH 7.4, preferably at least twice, and preferably for about 5 min per rinse.

If antibody is not directly conjugated to electron transfer agent, i.e., in an indirect method, the section is then incubated with a solution of about 10 ug/ml of second antibody, again for a time and temperature similar to the first incubation, followed by rinses. It is advantageous, when second antibody is used, to pretreat the section with normal serum from the same species as that used to raise the antibodies, diluted about 1:10 with PBS, to prevent non-specific binding of the conjugated antibodies.

The staining solution normally comprises a soluble reducing or oxidizing agent, e.g., NADH, in a concentration sufficient to rapidly and substantially quantitatively reduce or oxidize the electron transfer agent bound to the site of antibody specific binding A concentration of about 7 mg/ml of NADH is advantageously used, although higher or lower concentrations, e.g., about 0.1–50 mg/ml, preferably about 3–10 mg/ml, can be used with acceptable results. Also present in the staining solution is a soluble chromogen, e.g., nitro blue tetrazolium (NBT), normally in buffer, e.g., about 0.1 Tris/HCl, pH 7.5, at a chromogen concentration of about 0.1–50 mg/ml, preferably about 0.5–1.0 mg/ml, more preferably about 0.7 mg/ml. Other buffers can also be used, e.g., HEPES, MES, TES, MOPS, glycylglycine, Tris/maleate, phosphate, phosphate-citrate, maleatecacodylate, barbital and the like, and pH ranges of about 6 to about 9.5, preferably about 7 to 8.

The section is incubated in the staining solution for about 30 min, at about 37° C., in the dark, then raised with buffer, e.g., twice with PBS, at 5 min per rinse, and preferably counterstained with, e.g., nuclear fast red or hematoxylin, in order to better evaluate the histologic morphology. Slides can be permanently stored using graded alcohol and xylene dehydration and Permount mounting.

The method of the invention permits staining with increased sensitivity and reduced background staining, at least in part because the electron transfer agent is bound to the binding site of the specific antibody and cannot diffuse away and reduce the chromogen at a site remote from the morphologically significant antigen on the tissue section.

Immunohistochemical kits for staining tissue sections according to the method of the present invention will normally comprise one or more specific antibodies, either in the form of conjugates with electron transfer agent or an oligomeric carrier bearing a plurality of electron transfer agent molecules, or with biotin or other such component of a specific binding couple, or in unconjugated form. The specific antibodies can be lyophilized and supplied with separate buffer for reconstitution, or they can be supplied as solutions in an appropriate concentration or as a concentrate. Bridging antibodies and/or antibody conjugates and/or other specific binding couples or components thereof will also normally be present in such kits, again in lyophilized or dissolved form. Dry or dissolved soluble reducing or oxidizing agents, and dry or dissolved dhromogen will also normally be provided as kit components, either in the same container or in separate containers. Auxiliaries, such as additional buffer for rinsing, hematoxylin or other counterstain, normal serum and the like, can also be included in the kits.

Kit components can be packaged in amounts suitable for staining one or only a few slides or in larger amounts for bulk solution preparation. In those embodiments wherein universal color developing agents are used, it is advantageous to package them in bulk for use with a variety of specific antibodies. In the event that components for use in the present method are separately available commercially, e.g., biotinylated anti-species antibodies, these components can conveniently be omitted from kits and supplied by the user. Moreover, where the user has access to the specific antibodies, the kit may contain only a bound form of the electron transfer agent, e.g., bound to second antibody, bound to a biotinylated oligomer, or in the form of an immune complex, e.g., poly(phenazine-carboxyllysine)/anti-phenazine, and optionally the soluble redox agent and chromogen.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example, all temperatures are set forth uncorrected in degrees Celsius; unless otherwise indicated, all parts and percentages are by weight.

EXAMPLE 1

Charging oligomer with electron transfer agent

A solution of 11 mg (0.032 mmol) of 2-carboxyphenazine methosulfate (CPMS) in 3 ml of dry dimethylsulfoxide (DMSO) is treated with 6.6 mg (0.032 mmol) of dicyclohexylcarbodiimide, and the resultant mixture is stirred for 2 hrs, at ambient temperature, in a nitrogen atmosphere. The activated CPMS is treated with a solution of 10 mg (0.625 umol) of poly-L-lysine (PLL, average m.w. of about 16,000 daltons), in 1 ml dry DMSO containing 75 ul of triethylamine, and the resultant solution is stirred for an additional 2 hrs at ambient temperature. The precipitated dicyclohexylurea is removed by filtration, and the CPMS-charged PLL is purified by chromatography on a Bio-Gel P-6DG silica gel column (1.5×50 cm) which has been equilibrated with HEPES buffer, pH 7.5. The fractions containing CPMS-PLL conjugate are pooled and lyophilized. The crude lyophilizate can be used for subsequent steps without further purification.

EXAMPLE 2

Derivitization of the charged oligomer

The crude lyophilizate of CPMS-PLL conjugate, prepared according to Example 1 hereof, is redissolved in 2 ml of distilled water, and the pH is adjusted to 7.5 with either 0.05M HCl or NaOH. To the resultant solution is added 50 ul of a solution of 1.7 mb/ml of 2-iminothiolane (methyl-4-mercaptobutyrimidate) in dry DMSO, and the resultant solution is allowed to react for about 60 min, at ambient temperature, in a nitrogen atmosphere. The reaction mixture is then applied to a column of BioGel P-6DG (1×50 cm) which has been equilibrated with PBS, pH 7.2 (0.01M phosphate), containing 0.001M sodium ascorbate, and the fractions containing thiolated product are pooled and purified, e.g., by lyophilization and chromatography. The crude lyophilizate from this step can be used without further purification for subsequent steps.

EXAMPLE 3

Maleimido specific antibody

A solution of 5 mg (0.32 nmol) of an anti-CEA monoclonal IgG, e.g., the NP-2 monoclonal disclosed in U.S. Ser. No. 633,999, in 1 ml of HEPES buffer, pH 7.5, is mixed with 50 ul of a solution of 2.7 mg/ml (6.45 umol) of m-maleimidobenzoylsulfosuccinimide ester in dry DMSO. The reaction is effected for about 60 min, at ambient temperature, and the resultant maleimide-containing antibody conjugate is purified on a column of BioGel P-6DG (1×30 cm) which has been equilibrated with PBS, pH 7.2 (0.01M phosphate). The fractions containing the antibody conjugate are pooled and concentrated to about 1 ml by means of a Centricon 30 membrane. The concentrate is suitable for use in the next step without further purification.

EXAMPLE 4

Antibody-electron transfer agent conjugate

The concentrate produced in Example 3 hereof is mixed with the crude lyophilizate of thiolated CPMS-PLL conjugate produced according to Example 2 hereof, and the resultant solution is stirred for about 60 min, at ambient temperature. Unreacted maleimide groups are blocked by addition of 100 ul (0.3 umol) of 1M dithiothreitol in PBS, pH 7.2. The resultant antibody-CPMS-PLL conjugate is purified by gel filtration on a column of Sephacryl S-300 (2.6×100 cm) which has been equilibrated with PBS, pH 7.2. The resultant purified product fractions are pooled and lyophilized. The lyophilizate is suitable for use in a staining kit, but can be further purified by conventional antibody purification techniques if desired.

It will be apparent to the skilled artisan that the foregoing techniques are readily adapted to making conjugates of second antibody with the electron transfer agent, to permit a universal developing system to be used.

EXAMPLE 5

Direct Staining

A sample of colonic tissue obtained from a surgical specimen removed from a colon cancer patient is fixed in 10% buffered formalin and embedded in paraffin. Serial sections about 5 nm thick are prepared, and these are deposited on slides for immunohistochemical development. The slides are incubated for 20 min, at 37° C. in a solution containing 10 ug/ml of an antibody conjugate prepared according to Examples 1–4 hereof, using NP-2 anti-CEA murine monoclonal IgG, conjugated to a CPMS-PLL oligomeric conjugate or carboxylphenazine methosulfate and polylysine, linked to the antibody by means of thioether linkages. The antibody conjugate is dissolved in PBS.

After the antibody incubation, the slides are rinsed twice with PBS for 5 min per rinse. The rinsed slides are then incubated in the dark for 30 min, at 37° C., in a staining solution which contains 7 mg/ml of NADH and 0.7 mg/ml of NBT in 0.1MTris/HCl buffer, pH 7.5. After two 5 min rinses with PBS, the slides are counterstained with nuclear fast red, dehydrated with alcohols and xylene, and mounted in Permount (Fischer Scientific, Fairlawn, N.J.).

The blue formazan stain reveals at least equivalent morphology to that obtained with glucose oxidase staining or GAG staining, but requires only a single antibody incubation step, and is not highly sensitive to tetrazolium salt concentration or time of addition. Sensitivity and specificity are comparable, and definition of morphological features is sharp.

EXAMPLE 6

Universal antibody conjugate

Donkey anti-goat IgG is conjugated to the CPMS-PLL charged oligomer of Example 2 by reacting the antibody as in Example 3 to form a maleimido antibody, and reacting this derivative with the charged, thiolated oligomer to form the antibody conjugate. The conjugate is lyophilized for use in a staining kit.

EXAMPLE 7

Indirect staining

Affinity purified goat anti-CEA IgG is dissolved in PBS, pH 7.4, at a concentration of 10 ug/ml. Slides of colon tissue are prepared as in Example 5 hereof, and incubated in the specific antibody soltion for 20 min, at 37° C., then rinsed twice with PBS for 5 min per rinse. The slides are then pre-treated by incubating them in 1:10 normal donkey serum:PBS for 10 min, at 37° C., followed by one rinse with PBS. The pre-treated slides are then incubated with the donkey anti-goat IgG conjugate prepared according to Example 6 hereof, and dissolved in PBS, pH 7.4, for 30 min, at 37° C., rinsed twice with PBS, and developed according to the procedures of Example 5 hereof. Again, the results are at least equivalent to those obtained by classical glucose oxidase or GAG methods.

EXAMPLE 8

Staining kits

A non-enzymatic immunohistochemical direct staining kit is prepared, containing:
- a vial of lyophilized murine monoclonal anti-CEA NP-2 conjugated to a CPMS-PLL charged oligomer according to Example 4 hereof;
- a container of PBS, pH 7.4;
- a container of 0.1M Tris/HCl buffer, pH 7.5;
- a vial of NADH;
- a vial of NBT; and
- a vial of nuclear fast red.

An indirect non-enzymatic immunohistochemical staining kit is prepared which differs from the above direct kit in that the monoclonal anti-CEA conjugate is replaced by lyophilized affinity purified goat anti-CEA IgG; and the kit further contains a vial of lyophilized donkey anti-goat IgG-CPMS-PLL conjugate according to Example 6 hereof. It will be appreciated that the anti-CEA IgG can be replaced by anti-AFP IgG, anti-beta-HCG IgG, anti-CSAp IgG, anti-PAP IgG and the like, or that vials of these specific antibodies can also be added to this kit and used with the same universal developing system according to the method of Example 7 hereof.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In an immunohistochemical method for staining a histology or cytology specimen to reveal the presence therein of at least one immunologically detectable antigen, wherein (1) said specimen is contacted with a solution of a primary antibody or antibody fragment which specifically binds to said antigen, (2) unbound primary antibody or antibody fragment is removed, and (3) the presence of bound primary antibody or antibody fragment is revealed as a stain by reaction with a staining reagent system capable of transforming a chromogen to a colored dye which precipitates at the site of the bound primary antibody or antibody fragment, the improvement wherein said primary antibody or antibody fragment is directly or indirectly conjugated, or linked through one or more bridging antibodies or other specific binding couples, to an electron transfer agent capable of transforming said chromogen to said dye in the presence of a soluble oxidizing or reducing agent; and wherein the staining reaction effected by said staining reagent system is effected without the use of an enzyme.

2. The method of claim 1, wherein said antigen is a tumor-specific or tumor-associated antigen.

3. The method of claim 2, wherein said antigen is carcinoembryonic antigen, colon-specific antigen-p, human chorionic gonadotropin or its beta-subunit, alpha-fetoprotein or prostatic acid phosphatase.

4. The method of claim 1, wherein said antigen is a normal histological structure.

5. The method of claim 1, wherein said antigen is a viral, bacterial, fungal or parasitic antigen.

6. The method of claim 1, wherein said electron transfer agent is a substituted or unsubstituted phenazine.

7. The method of claim 6, wherein said phenazine has the formula

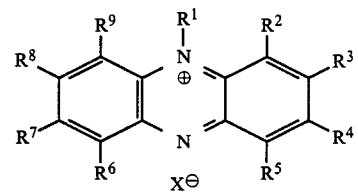

wherein $R^1$ is alkyl, cycloalkyl, aralkyl or L; X is one equivalent of a counteranion; $R^2$–$R^9$ are each independently H, alkyl, cycloalkyl, aryl, aralkyl, alkaryl, OH, $OR^1$, SH, CN, $NH_2$, $NHR^1$, $NR^1_2$, $NO_2$, F, Cl, Br, I, $SO_3$, $COOR^1$, or $R^2$ and $R^3$, $R^3$ and $R^4$, $R^4$ and $R^5$, $R^6$ and $R^7$, $R^7$ and $R^8$, or $R^8$ and $R^9$, taken together with the carbon atoms to which they are joined form a benzene ring, or one of $R^2$–$R^9$ is L; and L is a divalent linking function joining the phenazine ring system to said primary antibody or to said bridging antibody or specific binding couple component, or to an oligomeric carrier which is a component of an immune complex.

8. The method of claim 7, wherein said phenazine is N-methylphenazonium methosulfate, linked through a divalent linker function L comprising a thioether, amino, carboxyl or isothiocyanate derived function.

9. The method of claim 1, wherein said chromogen is a water-soluble tetrazolium salt capable of reduction to an insoluble formazan dye.

10. The method of claim 1, wherein said electron transfer agent is conjugated to a second antibody or antibody fragment which specifically binds a primary antibody or antibody fragment at a site which does not compromise its immunoreactivity, said primary antibody or antibody fragment being one which specifically binds said cellular component.

11. The method of claim 10, wherein said primary antibody or antibody fragment is a murine monoclonal antibody, and said electron transfer agent is conjugated to an anti-mouse antibody or antibody fragment.

12. The method of claim 1, wherein a plurality of molecules of said electron transfer agent are bound to an oligomer which is capped with biotin; and wherein avidin is conjugated to a second antibody or antibody fragment which specifically binds a primary antibody or antibody fragment at a site which does not compromise its immunoreactivity, said primary antibody or antibody fragment being one which specifically binds said cellular component.

13. The method of claim 12, wherein said oligomer is an oligopeptide comprising a plurality of lysine residues.

14. The method of claim 1, wherein a plurality of molecules of said electron transfer agent are bound to an oligomer to form an antigen; wherein said antigen is supplied to the staining system as a soluble immune complex with a tertiary antibody or antibody fragment which specifically binds to said antigen and which is derived from the same species as said primary antibody or antibody fragment; and wherein said immune complex is incubated with bound primary antibody or antibody fragment which has been incubated with a secondary antibody or antibody fragment which specifically binds the species of antibody or antibody fragment which the primary and tertiary antibody or antibodies fragments belong.

15. An enzyme-free immunohistochemical staining kit for staining histology or cytology specimens, comprising in suitable containers (A) at least one primary antibody or antibody fragment which specifically binds at least one immunologically detectable antigen whose presence in said specimen is to be detected and visualized;

(B) an electron transfer agent capable of transforming a soluble chromogen to an insoluble dye in the presence of a soluble oxidizing or reducing agent, said electron transfer agent being directly or indirectly conjugated to said antibody or antibody fragment, or to a second antibody or antibody fragment which specifically binds to said primary antibody at a site which does not comprise its immunological reactivity, or to another carrier capable of linking with said primary antibody through the intermediacy of one or a plurality of specific binding couples;

(C) a soluble chromogen; and (D) a soluble oxidizing or reducing agent; wherein the amounts of said antibody or antibody fragment, electron transfer agent, chromogen and oxidizing or reducing agent are each sufficient to enable said antigen to be stained if present in said specimen.

16. The kit of claim 15, wherein said primary antibody or antibody fragment specifically binds a tumor-specific or tumor-associated antigen.

17. The kit of claim 16, wherein said antigen is carcinoembryonic antigen, colon-specific antigen-p, human chorionic gonadotropin or its beta-subunit, alpha-fetoprotein or prostatic acid phosphatase.

18. The kit of claim 15, wherein said antigen is a normal histological structure.

19. The kit of claim 15, wherein said antigen is a viral, bacterial fungal or parasitic antigen.

20. The kit of claim 15, wherein said electron transfer agent is covalently linked to said primary antibody or antibody fragment.

21. The kit of claim 15, wherein said electron transfer agent is covalently linked to a second antibody or antibody fragment which specifically binds said primary antibody or antibody fragment.

22. The kit of claim 15, wherein said electron transfer agent is a substituted or unsubstituted phenazine; and wherein said chromogen is a watersoluble tetrazolium salt capable of reduction to an insoluble formazen dye.

23. The kit of claim 22, wherein said phenazine has the formula

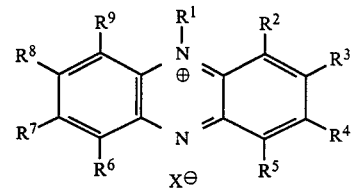

wherein $R^1$ is alkyl, cycloalkyl, aralkyl or L; X is one equivalent of a counteranion; $R^2$-$R^9$ are each independently H, alkyl, cycloalkyl, aryl, aralkyl, alkaryl, OH, $OR^1$, SH, CN, $NH_2$, $NHR^1$, $NR^1_2$, $NO_2$, F, Cl, Br, I, $SO_3$, $COOR^1$, or $R^2$ and $R^3$, $R^3$ and $R^4$, $R^4$ and $R^5$, $R^6$ and $R^7$, $R^7$ and $R^8$, or $R^8$ and $R^9$, taken together with the carbon atoms to which they are joined form a benzene ring, or one of $R^2$-$R^9$ is L; and L is a divalent linking function joining the phenazine ring system to said primary antibody or to said briding antibody or specific binding couple component, or to an aligomeric carrier which is a component of an immune complex.

24. The kit of claim 21, wherein said primary antibody or antibody fragment is a murine monoclonal antibody, and said electron transfer agent is conjugated to an anti-mouse antibody or antibody fragment.

25. The kit of claim 23, wherein said phenazine is N-methylphenazonium methosulfate.

* * * * *